United States Patent [19]
Himmelsbach et al.

[11] Patent Number: 6,143,317
[45] Date of Patent: Nov. 7, 2000

[54] ACTIVE SUBSTANCE PLASTERS

[75] Inventors: Peter Himmelsbach, Buxtehude; Peter Jauchen, Hamburg; Katharina Broschk, Hamburg; Ulrich Köhler, Hamburg; Matthias Wasner, Hamburg, all of Germany

[73] Assignee: Beiersdorf AG, Hamburg, Germany

[21] Appl. No.: 09/175,160

[22] Filed: Oct. 19, 1998

[30] Foreign Application Priority Data

Nov. 8, 1997 [DE] Germany ............................ 197 49 467

[51] Int. Cl.⁷ ................................ B32B 7/12; A61K 9/70
[52] U.S. Cl. .................... 424/443; 428/355 BL; 424/446; 424/447; 424/448; 424/449
[58] Field of Search ...................... 428/355 BL; 424/443, 424/445, 446, 447, 448, 449

[56] References Cited

U.S. PATENT DOCUMENTS

| | | | |
|---|---|---|---|
| 5,065,752 | 11/1991 | Sessions et al. | 128/156 |
| 5,362,496 | 11/1994 | Baker et al. | 424/435 |
| 5,389,168 | 2/1995 | Litchholt et al. | 156/77 |
| 5,618,899 | 4/1997 | Appelt et al. | 526/264 |

FOREIGN PATENT DOCUMENTS

| | | | |
|---|---|---|---|
| 0633789B1 | 1/1995 | European Pat. Off. | A61L 15/26 |
| 1942875 | 8/1972 | Germany | C09J 3/12 |
| 4416927 | 8/1985 | Germany . | |
| 4242015A1 | 10/1993 | Germany | A61L 15/26 |
| 19620107A1 | 11/1997 | Germany | C09J 7/04 |
| 19620109A1 | 11/1997 | Germany | C09J 7/04 |
| 1318916 | 5/1973 | United Kingdom | C08F 1/16 |
| 9743992 | 11/1997 | WIPO | A61F 13/02 |
| 9743993 | 11/1997 | WIPO | A61F 13/02 |

OTHER PUBLICATIONS

Derwent Abstract of DE4416927 (Aug. 31, 1995).
Derwent Abstract of Japan 57139347A (Aug. 28, 1992).
English–language counterpart to DE 19620109A1 and WO 9743992 (Specification—U.S. Serial Number unknown).
English–language counterpart to DE 19620107A1 and WO 9743993 (Specification—U.S. Serial Number 09/171,175 filed Oct. 14, 1998).

*Primary Examiner*—Daniel Zirker
*Attorney, Agent, or Firm*—Norris, McLaughlin & Marcus, P.A.

[57] ABSTRACT

Active substance plasters comprising a backing material and, applied at least partially thereon, an adhesive composition, wherein
 a) the adhesive composition comprises at least on active substance,
 b) the adhesive composition is a hotmelt adhesive composition, and
 c) the adhesive composition is foamed.

18 Claims, No Drawings

ACTIVE SUBSTANCE PLASTERS

The invention relates to active substance plasters comprising a backing material and, applied at least partially thereon, an adhesive composition comprising the one or more active substances to be delivered to the skin.

Transdermal therapeutic systems (TTS) are forms of administration of medicaments which deliver one or more medicaments to the skin over a defined period at their location of use. A distinction is made here between systemic and local administration forms.

With systemic administration forms, the active substance passes through the skin into the bloodstream by diffusion and can act within the body as a whole. Local administration forms, on the other hand, act only at the sites of application. The active substance remains in the skin or in the underlying layers.

Strongly adhering plasters are normally coated over their entire area with a zinc-rubber adhesive composition. The sticking of such products to the skin gives rise, following their removal, to marked skin irritation and mechanical stressing of the skin. Without auxiliary media, it is impossible to break the bond painlessly.

In some cases, there are allergic reactions. Furthermore, the adhesive compositions used often lead to a transfer of composition onto the skin.

The use of skin-friendly adhesive compositions, such as acrylate adhesive compositions and hydrogels, is out of the question because of their low shear stability and tack. Improvement through aftertreatment, especially crosslinking, is possible although the result remains unsatisfactory as a whole. The proprioreceptive effect is less than that of systems with a zinc-rubber adhesive composition.

Other known adhesive systems based on conventional block copolymers are not skin-friendly, owing to the high level of addition of stabilizer, or because of the high cohesiveness they have been found suitable to date only for industrial applications; or, alternatively, they cannot be formulated for strong adhesion and sticking to the skin.

The abovementioned adhesive compositions are pressure-sensitive self-adhesive compositions, where the compositions may be present in a carrier matrix for processing. The term carrier matrix is understood to refer to common organic or inorganic solvents or dispersion media.

Systems without a carrier matrix are referred to as 100% systems and are likewise not unknown. They are processed in the elastic or thermoplastic state. A common mode of processing is that of the melt.

Pressure-sensitive hotmelt adhesive compositions of this kind have already been described in the prior art. They are based on natural or synthetic rubbers and/or other synthetic polymers.

An advantage of the 100% systems is that they avoid an operation of removing the carrier matrix, i.e. the auxiliary media, thereby raising the productivity of processing and at the same time reducing the expenditure on machinery and the energy costs. In addition, this reduces the occurrence of residues of the carrier matrix, which, in turn, is to the benefit of a reduction in the allergenic potential.

Because of their high level of hardness, sticking to the skin is a problem for such 100% systems.

It is also known to apply such self-adhesive compositions not only over the entire area but also in the form of a pattern of dots, for example by screen printing (DE-C 42 37 252), in which case the dots of adhesive can also differ in their size and/or distribution (EP-B 353 972), or by intaglio printing, in lines which interconnect in the longitudinal and transverse direction (DE-C 43 08 649).

The advantage of the patterned application is that the adhesive materials, given an appropriately porous backing material, are permeable to air and water vapour and, in general, are readily redetachable.

A disadvantage of this product, however, is that if the area covered by the adhesive film, which per se is impermeable, is too large there is a corresponding reduction in the permeability to air and water vapour, and the consumption of adhesive composition rises, and also, if the area covered by the adhesive film is small, the adhesion properties deteriorate, i.e. the product is detached too readily from the substrate, especially in the case of heavy, textile backing materials.

Numerous embodiments of active substance plasters have already been described in the prior art, some of which operate in accordance with the reservoir principle, where the active substance is delivered, for example, by way of a mane, in some cases also with a matrix system or with a relatively complex multilayer structure.

It is known, then, that the adhesive composition of the plaster can be employed as the matrix comprising active substance. In addition to self-adhesive compositions applied from solution, hotmelt self-adhesive compositions have also been proposed for this purpose, as for example in EP-A 663 431, EP-A 452 034, EP-A 305 757, DE-A 43 10 012, DE-A 42 22 334 and DE-C 42 24 325. The active substances listed in these documents, if named at all, are systemic ones.

As examples of Active substance plasters, mention may be made of the active substance plasters which aid the circulation, belonging to the group of locally active therapeutic systems. The use of such plasters is indicated for the treatment of rheumatic complaints, sciatica, lumbago, stiff neck, shoulder/arm pain and muscular strains and sprains, muscular aching, or muscle, joint and nerve pain in the region of the locomotor system.

Capsaicin, belladonna and nonivamide are known active substances in such locally acting, circulation-aiding plasters. Because of their use on the locomotor system they are in general required to adhere strongly. Usually, the plasters are coated over their full area with a resin-rubber adhesive composition which comprises the active substance.

However, plasters of this kind, which usually have to be applied over a relatively large area, in some cases exhibit distinct mechanical skin irritations after removal in the case of sensitive patients. In some cases there are allergic reactions. After a prolonged period of application, their removal is to some extent painful.

A further disadvantage of the known thermally active plasters with an adhesive composition based on natural rubber, which is applied in the form of a solution with organic solvents to the plaster backing, is the comparatively low rate of release of the active substance.

The abovementioned disadvantages, and further disadvantages, apply also to active substance plasters comprising substances other than those mentioned.

For instance, WO 94/02123 describes an active substance plaster based on pressure-sensitive hotmelt adhesive compositions and comprising low-melting and/or readily volatile active substances in a concentration of from 2.5 to 25% by weight. The polymers employed in that document are A-B-A triblock styrene-ethylene-butylene-styrene block copolymers which are notable for low initial tack and low bond strength on skin.

EP 0 663 431 A2, EP 0 443 759 A3, EP 0 452 034 A2 and U.S. Pat. No. 5,371,128 describe uses of pressure-sensitive hot-melt adhesives, based on silicone, with diverse additives and in differentiated forms of construction.

DE 43 10 012 A1 describes the construction of a dermal therapeutic system from meltable poly(meth)acrylate mixtures.

DE 43 16 751 C1 describes a multi-chamber system for administering active substances.

EP 0 439 180 describes an active substance plaster for administering tulobuterol.

EP 03 05 757 describes an active substance plaster for administering nicotine.

EP 03 05 758 describes an active substance plaster for administering nitroglycerine.

EP 03 05 756 describes a device for dispensing substances, and the preparation and use thereof.

DE 37 43 945 A1 describes a device for administering substances, and the process for preparing this device. In the case of the pressure-sensitive hotmelt adhesive composition described, which is based on SIS, the device is not self adhesive. The processing ranges indicated therein lie well below those of hotmelt adhesive compositions and for such described systems would not provide sufficient anchorage of the adhesive composition.

WO 96/22083 indicates a polyisobutylene adhesive for transdermal purposes, having a tackifier with a high glass transition point. The adhesive is not foamed.

JP 07-196505 describes the administration of indomethacin in hotmelt pressure-sensitive adhesives. In this case, a polyethylene foam is used as carrier material.

JP 59-155479 describes an adhesive composition which, based on an elastomer, reacts to give a crosslinked foam. No release of substances is described.

JP 08-092954 discloses a thermal wrapping which comprises a local anaesthetic. The adhesive composition used is not a pressure-sensitive or self-adhesive composition but is a laminate adhesive.

U.S. Pat. No. 5,389,168 discloses an adhesive foam which, however, is used exclusively as a laminate adhesive. The release of substances is not described.

The object of the invention was therefore to provide plasters which contain active substance and which, while avoiding the disadvantages known from the prior art, feature a high level of efficacy, i.e. a relatively high rate of release, and good skin compatibility coupled with good adhesion. In addition, they should be able to be prepared in a technically simple and environmentally compatible manner.

This object is achieved by active substance plasters according to claim 1. The subclaims relate to advantageous embodiments of the plasters of the invention. The invention also embraces processes for preparing such plasters.

The invention accordingly provides active substance plasters, comprising a backing material and, applied at least partially thereon, an adhesive composition, which are notable in that a) the adhesive composition comprises at least one active substance, b) the adhesive composition is a hotmelt adhesive composition, and c) the adhesive composition is foamed.

The quantitative concentrations of the active substance or substances in the adhesive composition lie preferably between 0.01 and 50% by weight, preferably from 0.1 to 20% by weight.

By active substances in the context of the present invention are meant chemical elements, organic and inorganic compounds which are able to migrate from the constituents of a generic plaster that comprise them and so bring about a desired effect. Among the fields of use of the plasters of the invention, human and veterinary medicine is of particular importance.

Typical substances which can in this case be administered by way of plasters prepared in accordance with the invention are: aceclidine, amfetaminil, amfetamine, amyl nitrite, apophedrine, atabrine, alprostadil, azulene, arecoline, anethole, amylene hydrate, acetylcholine, acridine, adenosine triphosphoric acid, L-malic acid, alimemazine, allithiamine, allyl isothiocyanate, aminoethanol, apyzine, apiole, azatadine, alprenolol, ethinazone, benzoyl peroxide, benzyl alcohol, bisabolol, bisnorephedrine, butacetoluide, benactyzine, camphor, colecalciferol, chloral hydrate, clemastine, chlorobutanol, capsaicin, cyclopentamine, clobutinol, chamazulene, dimethocaine, codeine, chlorpromazine, quinine, chlorothymol, cyclophosphamide, cinchocaine, chlorambucil, chlorphenesin, diethylethane, divinylethane, dexchlorpheniramine, dinoprostone, dixyrazine, ephedrine, ethosuximide, enallylpropymal, emylcamate, erythrol tetranitrate, emetine, enflurane, eucalyptol, etofenamate, ethylmorphine, fentanyl, fluanisone, guaiazulene, halothane, hyoscyamine, histamine, fencarbamide, hydroxycaine, hexylresorcinol, isoaminile citrate, isosorbide dinitrate, ibuprofen, iodine, iodoform, isoaminile, lidocaine, lopirine, levamisole, methadone, methyprylon, methylphenidate, mephenesin, methylephedrine, meclastine, methopromazine, mesuximide, nikethamide, norpseudoephedrine, menthol, methoxyfluran, methylpentinol, metixene, mesoprostol, oxytetracaine, oxyprenolol, oxyphenbutazone, oxyquinoline, pinene, prolintane, procyclidine, piperazine, pivazide, phensuximide, procaine, phenindamine, promethazine, pentetrazol, profenamine, perazine, phenol, pethidine, pilocarpine, prenylamine, phenoxybenzamine, Resochin, scopolamine, salicylic acid ester, sparteine, trichloroethylene, timolol, trifluoperazine, tetracaine, trimipramine, tranylcypromine, trimethadione, tybamate, thymol, thioridazine, valproic acid and verapamil, and also other active substances familiar to the skilled worker that can be absorbed through the skin, including mucosae. This list is of course not exhaustive.

The active substances are dispersed in the adhesive composition preferably in a thermal homogenizer, such as thermal mixers, thermal kneading apparatus, roll mills or screw systems. The active substance can be added to the ready-prepared adhesive composition. The active substance can also, for example, be incorporated into an intermediate stage or into the initial mixture.

As adhesive compositions it is possible with advantage to employ thermoplastic hotmelt self-adhesive compositions based on natural and synthetic rubbers and on other synthetic polymers such as acrylates, methacrylates, polyurethanes, polyolefins, polyvinyl derivatives, polyesters or silicones, with appropriate additives such as tackifier resins, plasticizers, stabilizers and other auxiliaries where necessary.

Their softening point should be higher than 50° C., since the application temperature is generally at least 90° C., preferably between 120 and 150° C. or, in the case of silicones, between 180 and 240° C. If desired, subsequent crosslinking by irradiation with UV or electron beams may be appropriate.

Hotmelt self-adhesive compositions based on block copolymers, in particular, are notable for their diverse possibilities for variation, since the targeted reduction in the glass transition temperature of the self-adhesive composition, as a consequence of the selection of the tackifiers, plasticizers and polymer molecule size and of the molecular distribution of the components employed, ensures the necessary bonding with the skin in a manner appropriate to their function, even at critical points in the human locomotor system.

The high shear strength of the hotmelt self-adhesive composition is achieved by the high cohesiveness of the polymer. The good tack results from the range of tackifiers and plasticizers employed.

For systems which adhere particularly strongly the hotmelt self-adhesive composition is based preferably on block copolymers, especially A-B or A-B-A block copolymers or mixtures thereof. The hard phase A is primarily polystyrene or its derivatives and the soft phase B comprises ethylene, propylene, butylene, butadiene, isoprene or mixtures thereof, in which case particular preference is given to ethylene and butylene or their mixtures.

However, polystyrene blocks may also be present in the soft phase B in an amount of up to 20% by weight. The overall proportion of styrene, however, should always be less than 35% by weight. Preference is given to styrene contents of between 5 and 30%, since a lower styrene content makes the adhesive composition smoother.

The controlled blending of diblock and triblock copolymers is particularly advantageous, preference being given to a proportion of diblock copolymers of less than 80% by weight.

In one advantageous embodiment the hotmelt self-adhesive composition has the composition indicated below:

| from 10 to 90% by weight of | block copolymers, |
| from 5 to 80% by weight of | tackifiers, such as oils, waxes, resins and/or mixtures thereof, preferably mixtures of resins and oils, |
| less than 60% by weight of | plasticizers, |
| less than 15% by weight of | additives, |
| less than 5% by weight of | stabilizers, and |
| from 0.01 to 10% by weight of | active substance or substances. |

The aliphatic or aromatic oils, waxes and resins used as tackifiers are preferably hydrocarbon oils, waxes and resins, the consistency of the oils, such as paraffinic hydrocarbon oils, or of the waxes, such as paraffinic hydrocarbon waxes, accounting for their favourable effect on bonding to the skin. Plasticizers used are medium- or long-chain fatty acids and/or their esters. These additions serve to establish the adhesion properties and the stability. If desired, further stabilizers and other auxiliaries are employed.

Filling the adhesive composition with mineral fillers, fibres or hollow or solid microbeads is possible.

The hotmelt self-adhesive composition has a softening point of more than 50° C., preferably from 70 to 220° C. and, with very particular preference, from 75 to 140° C.

The hotmelt self-adhesive compositions are preferably formulated such that at a frequency of 0.1 rad/s they have a dynamic-complex glass transition temperature of less than 10° C., preferably from 0 to −300° C. and, with very particular preference, from −6 to −250° C.

Plasters in particular are subject to stringent requirements in terms of the adhesion properties. For ideal application the hotmelt self-adhesive composition should possess a high tack. There should be functionally appropriate bond strength to the skin and to the reverse of the backing. So that there is no slipping, the hotmelt self-adhesive composition is also required to have a high shear strength.

The targeted reduction in the glass transition temperature of the self-adhesive composition, as a consequence of the selection of the tackifiers, of the plasticizers and of the polymer molecule size, and of the molecular distribution of the components employed, achieves the necessary bonding, appropriate to its function, with the skin and with the reverse of the backing.

The high shear strength of the self-adhesive composition employed here is achieved by means of the high cohesiveness of the block copolymer. The good tack arises from the range of tackifiers and plasticizers employed.

Product properties such as tack, glass transition temperature and shear stability can be quantified readily using a dynamomechanical frequency measurement. In this case, use is made of a rheometer controlled by shearing stress.

The results of this measurement method give information on the physical properties of a substance by taking into account the viscoelastic component. In this instance, at a preset temperature, the hotmelt self-adhesive composition is set in oscillation between two plane-parallel plates with variable frequencies and low deformation (linear viscoelastic region). Via a pickup control unit, with computer assistance, the quotient (Q=tan δ) between the loss modulus (G", viscous component) and the storage modulus (G', elastic component) is determined.

$$Q = \tan\delta = G''/G'$$

A high frequency is chosen for t he subjective sensing of the finger tack (tack) and a low frequency for the shear strength.

A high numerical value denotes better tack and poorer shear stability.

The glass transition temperature is that temperature at which the amorphous or partially crystalline polymers undergo transition from the liquid or rubber-elastic state into the hard-elastic or glassy state or vice versa (Römpp Chemie-Lexikon, 9th ed. volume 2, page 1587, Georg Thieme Verlag Stuttgart—New York, 1990). It corresponds to the maximum of the temperature function at a predetermined frequency.

For medical applications in particular, a relatively low glass transition point is required.

| Designation | $T_G$ low frequency | Conformity low frequency/RT | Tack high frequency/RT |
| --- | --- | --- | --- |
| Hotmelt self-adhesive composition A | −12 ± 2° C. | tan δ = 0.88 ± 0.03 | tan δ = 0.84 ± 0.03 |
| Hotmelt self-adhesive composition B | −9 ± 2° C. | tan δ = 0.32 ± 0.03 | tan δ = 1.70 ± 0.03 |

Preference is given in accordance with the invention to hotmelt self-adhesive compositions for which the ratio of the viscous component to the elastic component at a frequency of 100 rad/s at 25° C. is greater than 0.7, preferably from 1.0 to 5.0, or to hotmelt self-adhesive compositions for which the ratio of the viscous component to the elastic component at a frequency of 0.1 rad/s at 25° C. is less than 0.6, preferably between 0.4 and 0.02 and, with very particular preference, between 0.3 and 0.1.

In order to ensure the use of the plasters in proper accordance with their function, the adhesive compositions are foamed.

In this case the adhesive compositions with the active substances added to them are preferably foamed using inert gases, such as nitrogen, carbon dioxide, noble gases, hydrocarbons or air, or mixtures thereof. In some cases, foaming additionally by thermal decomposition of gas-evolving substances, such as azo, carbonate and hydrazide compounds, has been found to be suitable.

The degree of foaming, i.e. the gas content, should be at least about 5% by volume and can range up to about 85% by volume. In practice, levels of from 10 to 75% by volume, preferably 50% by volume, have been found to be appropriate. Operating at a relatively high temperature of approximately 100° C. and with a comparatively high internal pressure produces very open-pored adhesive foam layers which are particularly permeable to air and water vapour.

The advantageous properties of the adhesive coatings of the invention, such as low consumption of adhesive, high tack and good conformity, even on uneven surfaces, owing to the elasticity and plasticity of the foamed adhesive compositions, and also the initial tack, can be utilized to best effect in the field of active substance plasters.

At the same time, the vacuoles in the foam bring about a more than proportional increase in the transportation of the active substances, as a result of which very good release rates are achieved.

A particularly suitable process for preparing the adhesive composition foamed in accordance with the invention operates by the foam mixing system. In this system, the thermoplastic adhesive composition is reacted with the intended gases, such as nitrogen, air or carbon dioxide, for example, in various volume proportions (from about 10 to 80% by volume) in a stator/rotor system under high pressure and at a temperature above the softening point (approximately 120° C.).

While the gas entry pressure is greater than 100 bar, the mixing pressures between gas and thermoplastic in the system are from 40 to 100 bar, preferably from 40 to 70 bar. The pressure-sensitive adhesive foam produced in this way can subsequently pass through a line into the applicator unit. In the applicator unit, commercially customary nozzles, extruder systems or chamber systems are used.

The interaction of the active substances with the skin is, as is known, modulated by enhancers that are mixed into the adhesive composition or intensified by the occlusive effect of adhesive composition and covering. In contrast to this it is possible, with the use of breathable doped coatings in conjunction with elastic and likewise breathable backing materials, in particular for example during sporting activities, to achieve a) a level of wear comfort which is perceived subjectively as more pleasant by the user and b) as a result of an interaction of the skin with the environment (for example suppression of perspiration) that is less disturbed by the release behaviour, a more defined penetration of active substances into the skin.

In contrast, by virtue of the processes mentioned here, it is also possible to achieve permeability of the doped plaster system from the outside. By virtue of this property of the product, therefore, it is possible following actual application for substances to be brought to the contact point between doped adhesive/skin, through the backing, even at a later time (sprinkling on of liquid, wiping, etc.). These substances might, for example, comprise an additional enhancer effect or might initiate or attenuate the pharmaceutical action or modulate appropriately for a favourable consumer response.

In order to emphasize the advantages of a foamed hotmelt self-adhesive composition relative to an unfoamed system, in addition, a number of series of experiments have been carried out in the shear stress-controlled rheometer. Various hotmelt self-adhesive compositions were chosen.

In this case, again, at a predetermined temperature, foamed and unfoamed hotmelt self-adhesive compositions were set in oscillation between two plane-parallel plates with variable frequencies and low deformation (linear viscoelastic region). Subsequently, with computer assistance, the quotient (Q=tan δ) between the loss modulus (G", viscous component) and the storage modulus (G', elastic component) was determined.

$$Q = \tan \delta = G''/G'$$

In the table below, hotmelt self-adhesive composition is abbreviated for simplicity to HMSA.

| Designation | Acrylate-based<br>HMSA A<br>Block copolymer-based<br>HMSA B and C<br>Conformity<br>low frequency/RT | Tack<br>high frequency/RT |
|---|---|---|
| HMSA A (unfoamed) | $\tan \delta = 0.35 \pm 0.05$ | $\tan \delta = 0.45 \pm 0.05$ |
| HMSA A foam volume ($N_2$) = 50% | $\tan \delta = 0.46 \pm 0.05$ | $\tan \delta = 0.65 \pm 0.05$ |
| HMSA A (unfoamed) | $\tan \delta = 0.45 \pm 0.05$ | $\tan \delta = 0.50 \pm 0.05$ |
| HMSA A foam volume ($N_2$) = 70% | $\tan \delta = 0.58 \pm 0.05$ | $\tan \delta = 0.68 \pm 0.05$ |
| HMSA B (unfoamed) | $\tan \delta = 0.15 \pm 0.05$ | $\tan \delta = 1.7 \pm 0.05$ |
| HMSA B foam volume ($N_2$) = 50% | $\tan \delta = 0.27 \pm 0.05$ | $\tan \delta = 1.85 \pm 0.05$ |
| HMSA C (unfoamed) | $\tan \delta = 0.16 \pm 0.03$ | $\tan \delta = 1.1 \pm 0.05$ |
| HMSA C foam volume ($N_2$) = 50% | $\tan \delta = 0.31 \pm 0.05$ | $\tan \delta = 1.25 \pm 0.05$ |

The results show a marked increase in the tan " values as a result of foaming, and thus a measurably better conformity and tack.

By virtue of the foaming of the adhesive composition and the open pores in the composition which form as a result, and given the use of an inherently porous backing, the products coated with the adhesive composition have good permeability to water vapour and air. The amount of adhesive composition required is considerably reduced without adverse effect on the adhesion properties. The adhesive compositions have a surprisingly high tack, since per gram of composition there is more volume and thus more adhesion surface for wetting of the substrate that is to be bonded, and the plasticity of the adhesive compositions is increased by the foam structure. Anchorage to the backing material is also improved by this means. The foamed adhesive coating, moreover, gives the products a soft and conforming feel.

Foaming also reduces the viscosity, in general, of the adhesive compositions. This lowers the melt energy, and even thermally unstable backing materials can be coated directly.

The product advantages as a result of foaming of the adhesive compositions, such as high bond strength and good air and water vapour permeability, can be inferred from the following measurements. In the measurements, plasters were coated with foamed and unfoamed hotmelt self-adhesive compositions respectively and were compared with one another.

EXAMPLE 1

Plasters with foamed hotmelt self-adhesive compositions adhere more strongly to the skin than plasters with unfoamed hotmelt self-adhesive compositions at the same application rate. Since bond strength on the skin varies from one skin type to the next, the unfoamed adhesive composition was given an index of 100 and the foamed plaster was related to this. This gave the following results:

Index=bond strength on the skin (foamed)/bond strength on the skin (unfoamed)

The table below shows the increase in bond strength on skin.

| Application rate | Woven (nonelast.) | Woven (elast.) | Nonwoven |
|---|---|---|---|
| 40 g/m$^2$ | | 105–110% | |
| 60 g/m$^2$ | | | 120–130% |
| 80 g/m$^2$ | | 110–125% | 110–120% |
| 120 g/m$^2$ | | 120–170% | |

EXAMPLE 2

Plasters with foamed hotmelt self-adhesive compositions are more permeable to air than plasters with unfoamed hotmelt self-adhesive compositions at the same application rate. The air permeability of plasters with unfoamed adhesive compositions was less than 1 cm$^3$/cm$^2$/s in the case of the samples examined. These air permeabilities relate to a degree of foaming of 50% in the end product.

The table below shows the air permeability as a function of application rate (in each case in cm$^3$/cm$^2$/s).

| Application rate | Woven (nonelast.) | Woven (elast.) unexpanded | Woven (elast.) expanded | Nonwoven |
|---|---|---|---|---|
| 40 g/m$^2$ | 6–19 | | | |
| 60 g/m$^2$ | | | | 90–100 |
| 80 g/m$^2$ | 3–8 | 20–35 | 90–110 | |
| 120 g/m$^2$ | 0.5–3 | | | |

EXAMPLE 3

The air permeability is dependent on the degree of foaming. The results were determined at an application rate of 80 g/m$^2$.

The table below shows the dependency of air permeability on the degree of foaming.

| Degree of foaming | Nonelast. woven |
|---|---|
| 30% | 2–5 cm$^3$/cm$^2$/s |
| 50% | 3–8 cm$^3$/cm$^2$/s |
| 70% | 7–25 cm$^3$/cm$^2$/s |

EXAMPLE 4

The permeability to water vapour is also of particular importance for the skin. Similar plasters with unfoamed hotmelt self-adhesive compositions are not permeable to water vapour. The samples presented were conditioned beforehand at 23.5° C. The exemplary test parameters are a temperature of 37° C., a saturation vapour pressure of 6.274 kPa and a relative atmospheric humidity of 30%.

The table below shows the water vapour permeability rate as a function of the application rate.

| Application rate | Woven (nonelast.) in g/m$^2$/24 h | Woven (elast.) unexpanded in g/m$^2$/24 h | Nonwoven in g/m$^2$/24 h |
|---|---|---|---|
| 40 g/m$^2$ | 1020 | | |
| 60 g/m$^2$ | | | 2740 |
| 80 g/m$^2$ | 520 | 2510 | |
| 120 g/m$^2$ | 138 | | |

EXAMPLE 5

The text below shows the dependency of the water vapour permeability on the degree of foaming. For this purpose an application rate of 80 g/m$^2$ was chosen. The parameters described in Example 4 were held constant.

The table below shows the water vapour permeability rate as a function of the degree of foaming.

| Degree of foaming | Nonelast. woven in g/m$^2$/24 h |
|---|---|
| 30% | 240 |
| 50% | 520 |
| 70% | 990 |

Samples with the same adhesive composition but without the latter being foamed are found to be impermeable or to have much lower permeabilities.

It is also advantageous, especially for use in medical products, if the foamed adhesive composition is applied partially to the backing material, for example by halftone printing, thermal screen printing, thermal flexographic printing or intaglio printing, because backing materials which have been self-adhesively treated in a continuous applied line may under adverse circumstances induce mechanical skin irritations when applied.

It is also possible, furthermore, to apply the adhesive composition, for example, by spraying, which produces a more or less irregular pattern of application.

Partial application makes it possible, through controlled channels, to dissipate the transepidermal water loss and improves the removal of sweat from the skin in vapour form, especially when the backing materials used are permeable to air and water vapour. By this means the skin irritations induced by accumulation of body fluids are avoided. The dissipation channels that have been setup enable fluids to be conducted away.

Preference is given to application in t he form of polygeometric domes, especially those where the ratio of diameter to height is less than 5:1. Printed application of other forms and patterns on the backing material is also possible—for example, a printed image in the form of alphanumeric character combinations or patterns such as matrices, stripes, assemblies of domes, and zigzag lines.

The foamed adhesive composition can be distributed uniformly over the backing material; alternatively, it can be applied with a thickness or density which varies over the area, as appropriate for the function of the product. Finally, the dome can also be applied at least in part to an adhesive area.

The principle of thermal screen printing consists in the use of a rotating, heated, seamless, drum-shaped, perforated, cylindrical screen which is fed via a nozzle with the preferred hotmelt self-adhesive composition. A specially shaped nozzle lip (circular- or square-section coating bar) presses the foamed hotmelt self-adhesive composition, which is fed in via a channel, through the perforation of the screen wall and onto the backing web that is conveyed past it. This backing web is guided by means of a counterpressure roller against the external jacket of the heated screen drum at a rate which corresponds to the peripheral speed of the rotating screen drum.

In this process, the formation of the small domes of adhesive takes place with the following mechanism:

The pressure of the nozzle coating bar conveys the foamed hotmelt self-adhesive composition through the screen perforation onto the backing material. The size of the domes formed is predetermined by the diameter of the screen perforation. The screen is lifted from the backing in accordance with the rate of transportation of the backing web (rotary speed of the screen drum). As a consequence of the high adhesion of the self-adhesive composition and of the internal cohesion of the hotmelt, the limited supply of hotmelt self-adhesive composition in the perforations is drawn in sharp definition from the base of the domes that is already adhering to the backing and is conveyed onto the backing by the pressure of the coating bar.

Following the end of this transportation, the more or less highly curved surface of the dome forms over the predefined base area in dependence on the rheology of the hotmelt self-adhesive composition. The height-to-base ratio of the dome depends on the ratio of the perforation diameter to the wall thickness of the screen drum and on the physical properties (flow behaviour, surface tension and contact angle on the backing material) of the self-adhesive composition.

For the screen in thermal screen printing, the web-to-hole ratio can be less than 3:1, preferably less than or equal to 1:1 and, in particular, equal to 1:3.

The above-described mechanism of formation of the domes requires, preferentially, backing materials that are absorbent or at least wettable by hotmelt self-adhesive composition. Non-wetting backing surfaces must be pretreated by chemical or physical methods. This can be effected by means of additional measures such as Corona discharge, for example, or by coating with substances which improve wetting.

Using the printing technique indicated it is possible to lay down the size and shape of the domes in a defined manner. The bond strength values which are relevant for use (determine the quality of the products formed) are within very narrow tolerances provided that coating is carried out correctly. The base diameter of the domes can be chosen from 10 $\mu$m to 5000 $\mu$m, the height of the domes from 20 $\mu$m to 2000 $\mu$m, preferably from 50 $\mu$m to 1000 $\mu$m, the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, harmonized with the various backing materials and applications.

The backing material is preferably coated at a rate of more than 2 m/min, preferably from 20 to 220 m/min, the chosen coating temperature being greater than the softening temperature.

The foamed hotmelt self-adhesive composition can be applied to the backing material with an areal weight of greater than 15 g/m$^2$, preferably between 30 and 400 g/m$^2$ and, with very particular preference, between 130 and 300 g/m$^2$.

The percentage area that is coated with the foamed hotmelt self-adhesive composition should be at least 20% and can range up to approximately 95%, for specific products preferably from 40 to 60% and from 70 to 95%. This can be achieved, if desired, by means of multiple application, with the possible use if desired of foamed hotmelt self-adhesive compositions having different properties.

The combination of the foamed hotmelt self-adhesive composition and the partial coating firstly ensures secure bonding of the medical product on the skin and secondly prevents at least visually discernible allergic or mechanical skin irritations, even in the case of an application which extends over several days.

The epilation of corresponding body regions and the transfer of composition to the skin are negligible owing to the high cohesiveness of the adhesive, since the adhesive is not anchored to skin and hair—rather, the anchorage of the adhesive composition to the backing material, at up to 15 N/cm (sample width), is good for medical applications.

Because of the intended breakage points that have been formed in the coating, layers of skin are no longer displaced with one another or against one another in the course of detachment. The non-displacement of the layers of skin and the relatively low level of epilation lead to an unprecedented degree of painlessness in such strongly adhering systems. In addition, the individual biomechanical control of bond strength, which exhibits a demonstrable reduction in the bond strength of these plasters, assists the detachability. The applied plaster shows good proprioreceptive effects.

Depending on the backing material and its temperature sensitivity, the foamed hotmelt self-adhesive composition can be applied directly or can be applied first to an auxiliary support and then to the ultimate backing. Subsequent calendering of the coated product and/or pretreatment of the backing, such as Corona irradiation, for better anchorage of the adhesive layer may also be advantageous.

In addition, treatment of the foamed hotmelt self-adhesive composition by electron beam post-crosslinking or by UV irradiation can lead to an improvement in the desired properties.

Suitable backing materials are all rigid and elastic sheetlike structures of synthetic and natural raw materials. Preference is given to backing materials which, following the application of the adhesive composition, can be employed in such a way that they fulfil the characteristics of a functional dressing.

Examples are textiles such as wovens, knits, lays, nonwovens, laminates, nets, films, foams and papers. In addition, these materials can be pretreated or aftertreated. Common pretreatments are Corona and hydrophobicization; customary aftertreatments are calendering, thermal conditioning, laminating, punching and covering.

The coated backing material with the foamed adhesive composition can have a permeability to air of greater than 1 cm$^3$/(cm$^2$*s), preferably greater than 15 cm$^3$/(cm$^2$*s) and, with very particular preference, greater than 50 cm$^3$/(cm$^2$*s), and a permeability to water vapour of greater than 500 g/(m$^2$*24 h), preferably greater than 1000 g/(m$^2$*24 h) and, with very particular preference, greater than 2000 g/(m$^2$*24 h).

Permeability to air and water vapour is maintained even in the case of a multi-ply bond.

Finally, following the coating operation, the plaster can be covered with an adhesive-repelling backing material, such as siliconized paper, or provided with a wound pad or with padding.

Subsequently, the plasters are punched out in the desired size.

It is particularly advantageous that the plaster can be sterilized, preferably by means of γ (gamma) radiation. Consequently, particular suitability for subsequent sterilization is possessed by block copolymer-based hotmelt self-adhesive compositions which contain no double bonds. This applies in particular to styrene-butylene-ethylene-styrene block copolymers or styrene-butylene-styrene block copolymers. In this case the adhesive properties are not subject to any changes significant for the application.

The plaster of the invention has a bond strength on the reverse of the backing of at least 1.5 N/cm, in particular a bond strength of between 2.5 and 5 N/cm. Higher bond strengths may be achieved on other substrates.

The intention in the text below is to describe particularly advantageous plasters of the invention without thereby wishing unnecessarily to restrict the invention.

EXAMPLE 6

In accordance with the invention, a substance release device was produced which comprises a hyperaemic active substance. On the basis of its properties as described below, the device can be used for application as a rheumatic plaster which in addition, on the basis of the good adhesion properties, can be applied for a number of days to joints of the human locomotor system. The backing material consisted of a nonelastic cotton fabric having a maximum tensile strength of more than 80 N/cm and an expansion at maximum tension of less than 30%.

The composition of the hotmelt pressure-sensitive adhesive composition was as follows:

an A-B/A-B-A block copolymer consisting of hard and soft segments, with an A-B-A:A-B ratio of 2:1 and a styrene content in the polymer of 13 mol %; its proportion in the adhesive composition is 44% by weight (Kraton G)

a paraffinic hydrocarbon wax whose proportion in the adhesive composition is 52% by weight hydrocarbon resins, with a proportion of 3.5% by weight (Super Resin HC 140)

an anti-ageing agent, with a proportion of less than 0.5% by weight (Irganox 1010)

a hyperaemic active substance (nonylvanillamide), with a proportion of 1% by weight The components of the adhesive that were employed were homogenized in a thermal mixer at 185° C. for three hours. The active substance was added in the cooling phase at 130° C., and homogenization was continued in the mixer for 30 minutes.

The softening point of this adhesive composition was 85° C. (DIN 52011) and the adhesive composition had a viscosity of 2100 mPas at 150° C. (DIN 53018, Brookfield DV II, sp. 21). The glass transition by the above method was −9° C.

The doped hotmelt adhesive composition prepared in this way was foamed in a foam mixing apparatus from Nordson. The foaming gas used was nitrogen. The degree of foaming was 70% upstream of the applicator nozzle.

The self-adhesive composition was applied with a nozzle over the whole area of the backing. The direct coating operation took place at 50 m/min and at a temperature of 120° C. The backing material was coated with 170 g/m$^2$.

The plaster material produced in this way shows a comparably good release of the active substance (liberation study). After 24-hour application in vitro on pig skin, 15% of the plaster charge had been absorbed dermally.

The permeability to air of the treated backing material was 15 cm$^3$/(cm$^2$*s). Following application, no instances of skin irritation were found.

What is claimed is:

1. Active substance plasters, comprising a backing material which is at least partially coated with a foamed hotmelt adhesive composition containing
    at least one active substance.

2. Active substance plasters according to claim 1, wherein said active substance is present in an amount of from 0.01 to 50% by weight.

3. Active substance plasters according to claim 1, wherein said hotmelt adhesive composition is a self-adhesive hotmelt composition comprising a synthetic rubber selected from the group consisting of block copolymers, acrylates, methacrylates, polyurethanes, polyolefins, polyvinyl derivatives, polyacrylamides, polyesters and silicones.

4. Active substance plasters according to claim 3, wherein said synthetic rubber is an A-B block copolymer, an A-B-A block copolymer or a mixture thereof; phase A being primarily polystyrene or a polystyrene derivative and phase B being selected from the group consisting of ethylene, propylene, butylene, butadiene, isoprene and mixtures thereof.

5. Active substance plasters according to claim 4, wherein the overall proportion of styrene in the polymer is less than 35% by weight.

6. Active substance plasters according to claim 4, wherein the hotmelt self-adhesive composition is comprised of A-B/A-B-A block copolymers having a proportion of diblock copolymers of less than 80% by weight.

7. Active substance plasters according to claim 1, wherein the hotmelt self-adhesive composition comprises
    a) from 10 to 90% by weight of block copolymers,
    b) from 5 to 80% by weight of tackifiers,
    c) less than 60% by weight of plasticizers,
    d) less than 15% by weight of additives,
    e) less than 5% by weight of stabilizers, and
    f) from 0.01 to 10% by weight of active substance or substances.

8. Active substance plasters according to claim 1, wherein the hotmelt self-adhesive composition has a dynamic-complex glass transition temperature of less than 10° C. at a frequency of 0.1 rad/s.

9. Active substance plasters according to claim 1, wherein the degree of foaming of the hotmelt self-adhesive composition is at least 5% by volume.

10. Active substance plasters according to claim 1, wherein the adhesive composition is applied partially to the backing material by means of halftone printing, thermal screen printing, thermal flexographic printing or intaglio printing.

11. Active substance plasters according to claim 1, wherein the adhesive composition has been applied by spraying.

12. Active substance plasters according to claim 1, wherein the adhesive composition is applied in the form of polygeometric domes to the backing material.

13. Active substance plasters according to claim 1, wherein the adhesive composition has been applied to the backing material with an areal weight of greater than 15 g/m$^2$.

14. Active substance plasters according to claim 1, wherein at least 20% of the backing area is coated with the adhesive composition.

15. Active substance plasters according to claim 1, wherein the coated backing material has a permeability to air of greater than 1 cm$^3$/(cm$^2$*s), and a permeability to water vapor of greater than 500 g/(m$^2$*24 h).

16. Active substance plasters according to claim 1, wherein the plaster can be sterilized by means of $\gamma$ (gamma) radiation.

17. Active substance plasters according to claim 1, wherein the plaster has a bond strength on the reverse of the backing of at least 1.5 N/cm.

18. Active substance plasters according to claim 1, obtained by the foam mixing system technique.

* * * * *